United States Patent
Arseneau et al.

(10) Patent No.: US 8,369,928 B2
(45) Date of Patent: Feb. 5, 2013

(54) DATA PROCESSING SYSTEM FOR MULTI-MODALITY IMAGING

(75) Inventors: Roger E. Arseneau, Buffalo Grove, IL (US); James Frank Caruba, Bartlett, IL (US); Michael E. Casey, Louisville, TN (US); Mark Musrock, Oak Ridge, TN (US); Nan Zhang, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 344 days.

(21) Appl. No.: 12/564,635

(22) Filed: Sep. 22, 2009

(65) Prior Publication Data
US 2010/0076300 A1    Mar. 25, 2010

Related U.S. Application Data

(60) Provisional application No. 61/098,952, filed on Sep. 22, 2008.

(51) Int. Cl.
*A61B 5/05* (2006.01)
(52) U.S. Cl. ......... 600/411; 600/407; 600/410; 600/436
(58) Field of Classification Search .................. 600/407, 600/410, 411, 436; 324/318
See application file for complete search history.

(56) References Cited

U.S. PATENT DOCUMENTS

| | | | | |
|---|---|---|---|---|
| 4,939,464 A * | 7/1990 | Hammer | .................. | 324/318 |
| 5,524,629 A * | 6/1996 | Mahony | .................. | 600/454 |
| 5,672,877 A | 9/1997 | Liebig et al. | | |
| 2004/0027183 A1* | 2/2004 | Binkley | .................. | 327/172 |
| 2005/0113667 A1* | 5/2005 | Schlyer et al. | ................ | 600/411 |

OTHER PUBLICATIONS

Leroux et al. "Time Determination of BGO-APD Detectors by Digital Signal Processing for Positron Emissin Tomography." 2004. IEEE. pp. 1723-1727.*

* cited by examiner

*Primary Examiner* — James Kish
(74) *Attorney, Agent, or Firm* — Peter Kendall

(57) ABSTRACT

A data processing process and embodiment for optimizing the signal path for multi-modality imaging is described. The embodiment and process optimizes the signal to noise ratio in a positron emission tomography (PET) signal path utilizing scintillation crystals, avalanche photo diodes, and charge sensitive preamplifiers in a dual modality MRI/PET scanner. The dual use of both and analog pole zero circuit and a digital filter enables higher signal levels or a fixed ADC input range and thus a higher possible signal to noise ratio in the presence of significant pileup caused by high positron activity. The higher signal to noise ratio is needed in the PET signal architecture, because of the presence of non-modal time varying electromagnetic fields from the MR, which are a significant source of noise for the wideband PET signal modality.

36 Claims, 2 Drawing Sheets

DATA PROCESSING SYSTEM FOR MULTI-MODALITY IMAGING

CROSS-REFERENCE TO RELATED APPLICATIONS

This application claims benefit under 35 U.S.C. §119(e) to U.S. Provisional Patent Application Ser. No. 61/098,952, filed on Sep. 22, 2008, which is hereby incorporated by reference in its entirety.

FIELD OF THE INVENTION

The following relates to multi-modality tomographic imaging and more particularly to data processing systems for multi-modality imaging.

BACKGROUND OF THE INVENTION

Computed tomography (CT) is a medical imaging method or modality employing tomography, i.e., imaging by sections or sectioning, created by computer processing. Digital geometry processing can be used to generate a three-dimensional image of the inside of an object from a series of two-dimensional X-ray images taken around a single axis of rotation. CT data can be manipulated to demonstrate various bodily structures based on their ability to block an X-ray beam.

Magnetic Resonance Imaging (MRI) can provide more contrast between different soft tissues than CT, making it especially useful in neurological, musculoskeletal, cardiovascular, and oncological imaging. MRI employs radio frequency (RF) fields to alter the static magnet induced magnetic alignment of the subject nuclei, for example hydrogen atoms, in the subject to produce a rotating magnetic field. This field can be detected and used to produce images of the subject.

Positron emission tomography (PET) is a nuclear medicine imaging technique or modality, which can produce a three-dimensional image of functional processes in the body, for example the functioning of an organ. In PET, a radioactive tracer radioisotope is introduced into a subject, typically by injection. The positron emitting radioisotope occurs at a higher concentration in regions of high cellular metabolic activity. When an emitted positron encounters a free electron, the positron and electron may annihilate into two gamma photons which inherently provides higher signal to noise ratio than single photon emission imaging. These gamma photons can be detected by scintillation crystals, i.e., a material that emits light upon absorbing the gamma photons. The light emitted from the scintillation crystal can then be converted to electrical charge by an electronic light sensor, such as a photomultiplier tube (PMT) or avalanche photodiode (APD). The light sensor converts the light emitted by the scintillation crystal into a time varying stream of charge, i.e. an exponentially decaying current with decay time representative of the scintillation crystal. The resulting current produces a measurable electrical pulse; either current or impedance converted voltage may be used to measure the resulting total charge originating in the light sensor. Based on the time coincidence of the electrical pulses and the total energy measurements, three-dimensional images of the measured concentration of the tracer in the subject's body can be produced.

It can be beneficial to combine different modalities. For example, it can be beneficial to combine a CT scanner and a PET scanner in order to provide information about the functioning of an organ and information about the anatomical structures surrounding the organ. A scanner combining a CT modality and a PET modality can be referred to as a multi-modality scanner or a PET-CT scanner. A problem exists in multi-modality scanners, because multi-modality scanners require the signal architecture to accommodate concurrent operation of the modalities. Accommodation of concurrent operation of the modalities can result in less than optimized signal architectures for each individual modality.

The signal processing electronics used with the photo detectors in a commercial PET-CT scanner use vacuum tube based photomultiplier tubes (PMTs) to convert the light from individual scintillation crystals into electrical signals. However, for the development of a combined MRI-PET scanner, the photomultiplier tubes need to be replaced with another type of photo detector insensitive to the time varying electromagnetic fields of an MRI system. One candidate photodetector, which is MRI compatible, is an Avalanche photodiode (APD) biased in the linear range. The APD photo detector does not have the large signal gain achievable using photomultiplier tubes; typically PMTs are operated with anode gains on the order of $10^6$. Commercially available APDs used in PET detectors and are typically operated linearly with a much lower gain in the range of about 100 to 200.

A need exists, therefore, for a data processing system for multi-modality imaging. It would be desirable to provide a system, method and/or apparatus to optimize the signal gain from an Avalanche photodiode in an multi-modality MRI-PET scanner.

SUMMARY OF THE INVENTION

One embodiment relates to a method that can include scanning a subject with a combined magnetic resonance imaging (MRI)/positron emission tomography (PET) scanner, using an analog to digital converter to discrete time sample a signal from a photo detector, cancelling one or more poles of the signal with a digital infinite impulse response filter implemented with fixed-point arithmetic inside a field programmable gate array, and using the modified signal to generate an image of the subject. The signal can be approximated as a sum of exponentials. One or more of the one or more poles can remain uncancelled, and the method can further include using the uncancelled pole as an input to an algorithm. The algorithm can be a digitial timing algorithm, a crystal localization algorithm, and/or a total energy algorithm. One or more of the one or more poles can remain uncancelled when a detected photon count rate is greater than 50 kcps. The infinite impulse response filter z-transform for the field programmable gate array implemented single pole/zero digital filter can be described mathematically by the equation $$H(z) = K_1 - \frac{K_2}{1 - K_3 z^{-1}}$$

for an idealized model of a single exponential defined detector signal, wherein z represents the complex variable $e^{sT}$, $K_1$ represents a digital constant coefficient associated with the input, $K_2$ represents a digital constant coefficient, $K_3$ represents the coefficient associated with the past input and output samples. The photodetector can be an avalanche photodiode. The avalanche photodiode can be biased in the linear range. The method can further include measuring a signal tail remaining in the modified signal on a per photo detector basis or on a multiple combination of photo detectors basis, and using a least squares error fit of the measured signal to tune the digital coefficients of the digital infinite impulse response filter. The method can further include storing the tuned digital coefficients in nonvolatile memory or in volatile memory for later PET data acquisitions. Prior to using the analog to digital converter to discrete time sample the signal, the method can further include cancelling one or more poles of the signal with an analog pole/zero filter. The method can further include using a sum of exponentials approximation to model a remnant tail of the detector signal remaining after approximate analog pole/zero cancellation. The sum of exponentials approximation can use the predicted statistical mean or expected value of the integrator reset time constant of the application specific integrated circuit (ASIC) charge sensitive amplifier (CSA) as the analog pole/zero circuit time constant.

Another embodiment relates to a computer program product for a combined magnetic resonance imaging (MRI)/positron emission tomography (PET) scanner, the product can include: a computer-readable medium; a processing module residing on the computer-readable medium and operative to cancel one or more poles of a signal from a photo detector with a digital infinite impulse response filter implemented with fixed-point arithmetic and a display module residing on the computer-readable medium and operative to cause the display of an image of a subject based on the signal. The signal can be approximated as a sum of exponentials. One or more of the one or more poles can remain uncancelled, and the processing module can be further operative to use the resulting signal as an input to an algorithm. The algorithm can be a digitial timing algorithm, a crystal localization algorithm, and/or a total energy algorithm. One or more of the one or more poles can remain uncancelled when a detected photon count rate is greater than 50 kcps. The digital infinite impulse response filter can employ a z-transform described mathematically by the equation $$H(z) = K_1 - \frac{K_2}{1 - K_3 z^{-1}}$$

for an idealized model of a single exponential defined detector signal, wherein z represents the complex variable $e^{sT}$, $K_1$ represents a digital constant coefficient associated with the input, $K_2$ represents a digital constant coefficient, $K_3$ represents the coefficient associated with the past input and output samples. The photo detector can be an avalanche photodiode. The avalanche photodiode can be biased in the linear range. The processing module can be further operative to measure a signal tail remaining in the modified signal on a photo detector basis or on a multiple combination of photo detectors basis, and to use a least squares error fit to tune digital coefficients of the digital infinite impulse response filter. The processing module can be further operative to store the tuned digital coefficients in a nonvolatile or volatile memory for later PET data acquisitions.

Another embodiment relates to a system for a combined magnetic resonance imaginging (MRI)/positron emission tomography (PET) scanner, the system can include: a display device for displaying an image of a subject; a processor communicatively coupled to the display and operative to provide the image to the display device, wherein the processor cancels one or more poles of a signal from a photo detector with a digital infinite impulse response filter implemented with fixed-point arithmetic. The signal can be approximated as a sum of exponentials. One or more of the one or more poles can remain uncancelled, and the processor can be further operative to use the uncancelled pole as an input to an algorithm. The algorithm can be a digitial timing algorithm, a crystal localization algorithm, and/or a total energy algorithm. One or more of the one or more poles can remain uncancelled when a detected photon count rate is greater than 50 kcps. The digital infinite impulse response filter can employ a z-transform described mathematically by the equation $$H(z) = K_1 - \frac{K_2}{1 - K_3 z^{-1}}$$

for an ideal model of a single exponential defined detector signal, wherein z represents the complex variable $e^{sT}$, $K_1$ represents a digital constant coefficient associated with the input, $K_2$ represents a digital constant coefficient, $K_3$ represents the coefficient associated with the past input and output samples. The photo detector can be an avalanche photodiode. The avalanche photodiode can be biased in the linear range. The processor can be further operative to measure a signal tail remaining in the modified signal on a photo detector basis or on a multiple combination of photo detectors basis, and to use a least squares error fit to tune digital coefficients of the digital infinite impulse response filter. The processor can be further operative to store the tuned digital coefficients in a nonvolatile or volatile memory for later PET data acquisitions.

Many other aspects and examples will become apparent from the following disclosure.

BRIEF DESCRIPTION OF THE DRAWINGS

In order to describe various aspects, examples, and inventive embodiments, the following figures are provided.

Figure 1:
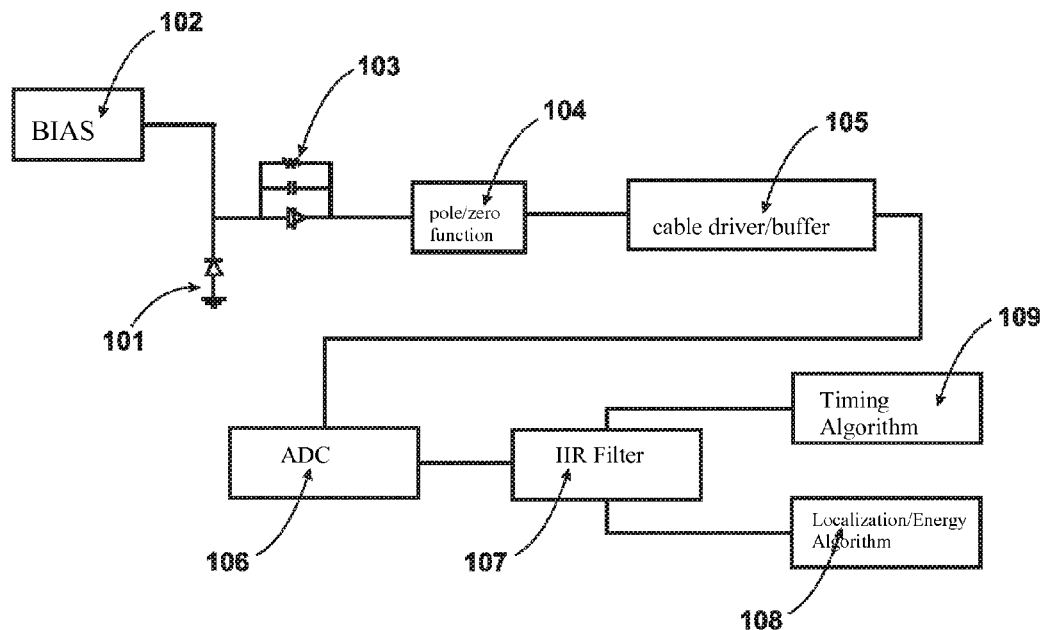
FIG. 1 depicts a block diagram of the electrical signal path of an APD based detector using an analog pole/zero circuit combined with a discrete infinite impulse response filter for approximate tail subtraction to improve high count rate operation with a limited analog to digital converter (ADC) input range.

It should be understood that the various embodiments are not limited to the arrangements and instrumentality shown in the drawings.

DETAILED DESCRIPTION OF THE INVENTION

The functions described as being performed at various components can be performed at other components, and the various components can be combined and/or separated. Other modifications can also be made.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. Numerical ranges include all values within the range. For example, a range of from 1 to 10 supports, discloses, and includes the range of from 5 to 9. Similarly, a range of at least 10 supports, discloses, and includes the range of at least 15.

Thus, the following disclosure describes data processing systems, methods, and apparatus for multi-modality imaging, including a system, a method, and an apparatus for optimizing the signal to noise ratio from an APD based detector in the presence of the time-varying electromagnetic field originating from the MRI modality. Many other examples and other characteristics will become apparent from the following description.

One embodiment relates to a signal processing system that can combine both analog and digital pole/zero circuits and processes for the PET electronics for a combined MR/PET modality. The system can be used in the field of nuclear medical imagining. The system can enable the signal processing hardware to achieve a higher count rate capability than systems employing either an analog circuit or a digital pole/zero filter algorithm employed individually.

The lower gain of the APDs requires the use of low noise electronics to be able to measure accurate timing of the annihilation photons for a PET modality. In the specific application where an analog charge sensitive amplifier (CSA) is used to integrate the APD charge derived from crystal scintillation light, an analog continuous reset of the integrator can be achieved by a large effective impedance in parallel with the integrating feedback element, a capacitor. This integrator's reset time can be set larger than the collection time both to measure the full photon yield and to minimize the current noise density due to the feedback impedance, $R_f$. From a macroscopic signal view, the end result with an APD/crystal-based detector and CSA is that an integral exponential rise is shorter than the reset time. This parallel resistor-capacitor (RC) results in an exponential signal tail necessarily much longer than that required to the measure the full light emission of the scintillation crystal. Although a gated low impedance reset circuit, i.e., a gated integrator, can be used to reduce the integrated charge signal, the gating logic contains higher frequency signal components that need to be shielded in this specialized application, since the PET detectors are in such close proximity to the receiving MR electronics and are a noise source for the MR modality that must be minimized. For low noise and simplicity for a large number of channels, the integration reset function for this application consists of an analog parallel RC.

Referring to FIG. 1, a block diagram of the electrical signal path of an avalanche photodiode based detector using an analog pole/zero circuit combined with a discrete infinite impulse response filter for tail subtraction to improve high count rate operation is depicted. Scintillation detector 101 with bias 102 generates an electrical signal. The signal is transmitted to analog charge-sensitive amplifier (CSA) circuit 103, which comprises an operational amplifier with passive feedback and gain elements. The analog pole/zero circuit 104 could be any of the recognized types that one of skill in the art could envision to effectively create, a circuit with one dominant pole and one dominant zero. Circuit 104 has a pole/zero function that can be given according to Equation 1 in its continuous Laplace Transform equivalent form.

$$\frac{s + \frac{1}{\tau_1}}{s + \frac{1}{\tau_2}}; \qquad \text{Equation 1.}$$

In Equation 1, s represents the continuous domain complex frequency variable σ+jω, $\tau_1$ represents [a single zero, pole cancellation constant, used to cancel the dominant signal tail from the CSA reset circuit, and $\tau_2$ represents the substituted circuit single pole time constant after the original pole from the reset circuit has been cancelled by zero, $\tau_1$.

Circuit 104 is connected to cable driver/buffer 105. The analog pole/zero cancelled signal is discrete-time sampled by analog to digital convert (ADC) 106. Digital IIR filter 107 can be used to improve the count rate performance of the crystal localization/energy algorithm 108 and timing algorithm 109 at high count rates. The localization routine is used to determine which crystal absorbed the gamma photons from a weighted combination of all light sensors associated with the APD/scintillation crystal detector. The number of crystals to light sensors in the APD/scintillation crystal detector is much greater than 1:1 for reasons of economic necessity. At a high detector count rate, signal tails from previously detected gamma photons are the source of measurement errors for determining event position, total event energy, and the gamma photon's time-of-arrival. The time-of-arrival circuit is used to determine if two detected gamma photons are in time coincidence of each other, on the order of 20 ns or less for modern PET scanners.

In nuclear spectroscopy, the exponential signal tail caused by an ideal integrator analog reset circuit can be eliminated by applying what is known as a pole/zero circuit in a following gain stages, which is shown in block diagram form in the first half of FIG. 1. If it is assumed that the scintillation detector signal is of first-order modeled as a signal exponential or pole of value $1/\tau_1$, the long tail resulting from the detector preamplifier can be cancelled by the zero of the pole/zero circuit leaving a remnant pole time constant $1/\tau_2$ of the pole/zero circuit. If the CSA is implemented in discrete form, the time constant of the resetting pole may be measured and an accurate cancellation is possible for a large number of channels. If the CSA is implemented in a custom application specific integrated circuit (ASIC), the reset time constant may be cancelled, not because the absolute time constants are known, but because the lithography and processing cause the component values of the capacitances and effective resistances of the integrator and pole/zero cancellation circuits to track within a small area even though the absolute values may deviate by as much as 50%.

According to one embodiment, discrete-time filters have been developed to emulate their analog continuous counterparts. The analog pole/zero filter described above may also be implemented as a discrete filter that is nearly equivalent to the time-sampled analog pole/zero impulse response given sufficient accuracy of the digital coefficients for the filter. The system can use a combination of analog and digital pole/zero processing to achieve the benefits of both methods when used in a distributed system for a combined MR/PET modality.

An advantage of an analog pole/zero cancellation directly at the detector before the signal is transmitted over a transmission cable to the processing unit is that the peak activity level that can be linearly processed with a fixed ADC analog input range is higher than if the detector signals are transmitted with slow exponential reset tails. If the long reset tail $\tau_1$ remains, then the photopeak signal needs to be appropriately scaled so that multiple pileup events do not cause the analog input range of the ADCs (typically 1 vpp or 2 vpp for a typical embodiment) to be exceeded. A pileup event is defined as a measured gamma photon event that contains at least some of the remnant energy of past scintillation events before previous scintillation events' signals have been reset to within 1% of the reference signal baseline level. The significance of the pileup events on the time-of-arrival and event localization measurement is best understood by modeling the input signals from the detectors as a random Poisson process in time.

If only the digital pole/zero is implemented directly from the CSA, the highest acceptable count rate is lower than if the digital pole/zero algorithm is combined with the analog pole/zero circuit. In practice, this may necessitate that the 511 Kev photopeak signal be lowered up to 5 times compared to an analog pole/zero filter applied to the APD detector signal prior to signal transmission as shown in FIG. 1. For a large distributed system this may cause distorted signals in the PET electronic signals due to the unrelated modality RF signals from the MR. There can be a remnant signal tail remaining from the analog pole/zero cancellation due to the component tolerances both in the CSA and in the analog pole/zero circuit.

Various embodiments of the system, method, and apparatus can use an analog pole/zero filter to allow an increased signal level at the interface between the PET detectors and processing unit in the PET modality of a combined MR/PET modality.

Various embodiments of the system, method, and apparatus can use a sum of exponentials approximation to model the remnant signal tail of the detector signal after the analog pole/zero cancellation. In the envisioned embodiment, the statistical mean or expected value of the single pole value of the Application Specific Integrated Circuit's (ASIC's) (CSA) reset time constant is used as the expected value of the pole time constant. The remnant signal tail resulting from AC coupling time constants and mismatch of the analog circuits can remain.

Various embodiments of the system, method, and apparatus can use a digitial infinite impulse response (IIR) filter implemented with fixed point arithmetic inside a field programmable gate array (FPGA) to cancel many poles of the signal approximated as a sum of exponentials, which is used as an input to a digital timing algorithm, crystal localization algorithm, and total energy algorithm. The embodiment will reduce measurement errors at single photons count rates of greater than 50 kcps. The analog pole/zero cancelled signal is discrete-time sampled by an ADC after appropriate Nyquist bandwidth limiting. The digital IIR filter is used to improve the count rate performance of the crystal localization and timing algorithms at greater than 50 kcps for the PET electronics in a dual mode MR/PET gantry.

Various embodiments can include a method that measures the remaining signal tail on a per signal basis during a routine gantry setup and use a least square error fit to tune the digital coefficients of the filter coefficients automatically during gantry setup to optimize the count rate capability of the PET signal path in the combined MR/PET gantry. The optimal coefficients can be determined at low system count rates, less than 20 kcps per signal, where the remnant signal tails can be minimized through an iterative process by acquiring a histogram of each signal tail, automatically readjusting the digital coefficients, followed by subsequent histogram periods. The coefficients are stored in nonvolatile memory for later PET data acquisitions scans at normal and high count rates.

The system, according to certain embodiments, is of particular use in a combined MR/PET modality where the narrowband MR electronics generate wideband electromagnetic signal content that is potentially coupled into different signal path points in the PET architecture. The system improves signal quality at the long cable interface and in the alter amplification stages.

The analog pole/zero filtered signals can have a higher bandwidth due to the substituted pole than the unfiltered CSA detector signals in order to improve the signal rise time and time resolution in the PET application. These higher frequency spectral components radiate more easily at the cable interface thus potentially impacting the MRI unless effective shielding is implemented.

Figure 2:
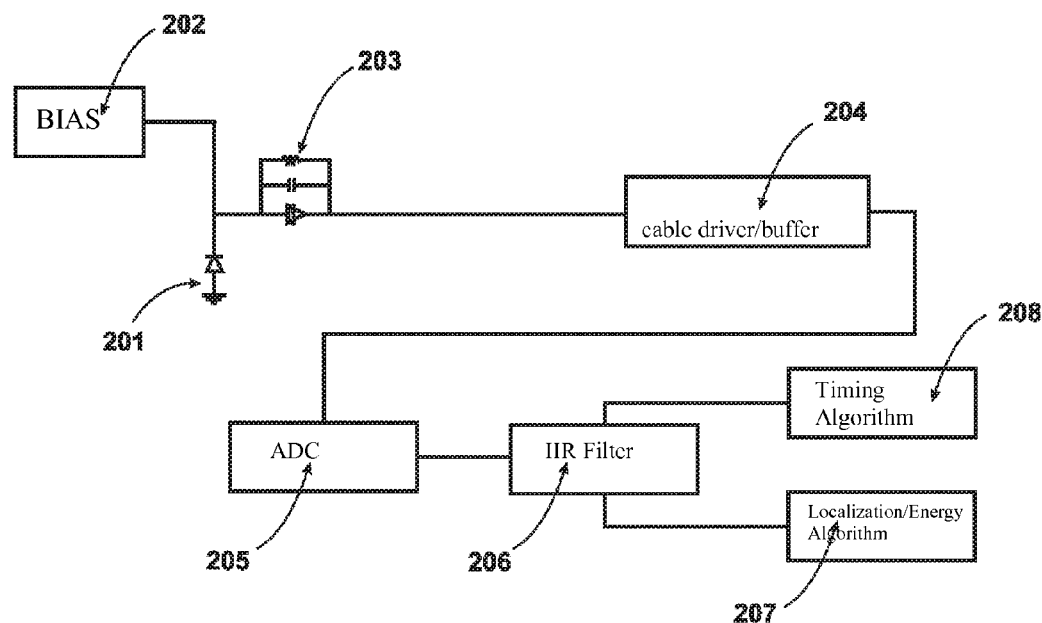
FIG. 2 depicts a block diagram of the electrical signal path of an avalanche photodiode based detector using a discrete infinite impulse response filter for tail subtraction to improve accuracy at moderate count rates.

Referring to FIG. 2, a block diagram of the electrical signal path of an avalanche photodiode based detector using a discrete infinite impulse response filter for tail subtraction to improve accuracy at moderate and high count rates is depicted. Scintillation detector 201 with bias 202 generates an electrical signal. The signal is transmitted to analog charge-sensitive amplifier (CSA) circuit 203, which comprises passive networks and an operational amplifier. Circuit 203 is connected to cable driver/buffer 204. The analog signal is discrete-time sampled by analog to digital converter (ADC) 205. Digital IIR filter 206 can be used to improve the count rate performance of the crystal localization/energy algorithm 207 and timing algorithm 208 at moderate and high count rates. Digital IIR filter 206 can be a single pole/zero digital filter and can comprise a field programmable gate array (FPGA) employing a z-transform filter described mathematically in the form of Equation 2, for an ideal single exponential defined signal originating from a CSA/scintillation crystal detector combination.

$$H(z) = K_1 - \frac{K_2}{1 - K_3 z^{-1}};$$  Equation 2.

In Equation 2, z represents the complex frequency variable $e^{sT}$, $K_1$ represents a constant coefficient, $K_2$ represents a scaling coefficient, $K_3$ represents the scaling filter coefficient associated with the last discrete output value of the IIR filter.

In the embodiment shown in FIG. 2, the system count rate is low enough that the dynamic range of the ADC is not approached at the scanner maximum count rate. The analog pole/zero circuit, at this point, becomes unnecessary, if the CSA integrator is assumed linear. The digitally implemented pole/zero filter is used to effectively cancel both the integrator circuit reset time and the AC coupling time constants from the APD/scintillation crystal based detectors.

Figure 3:
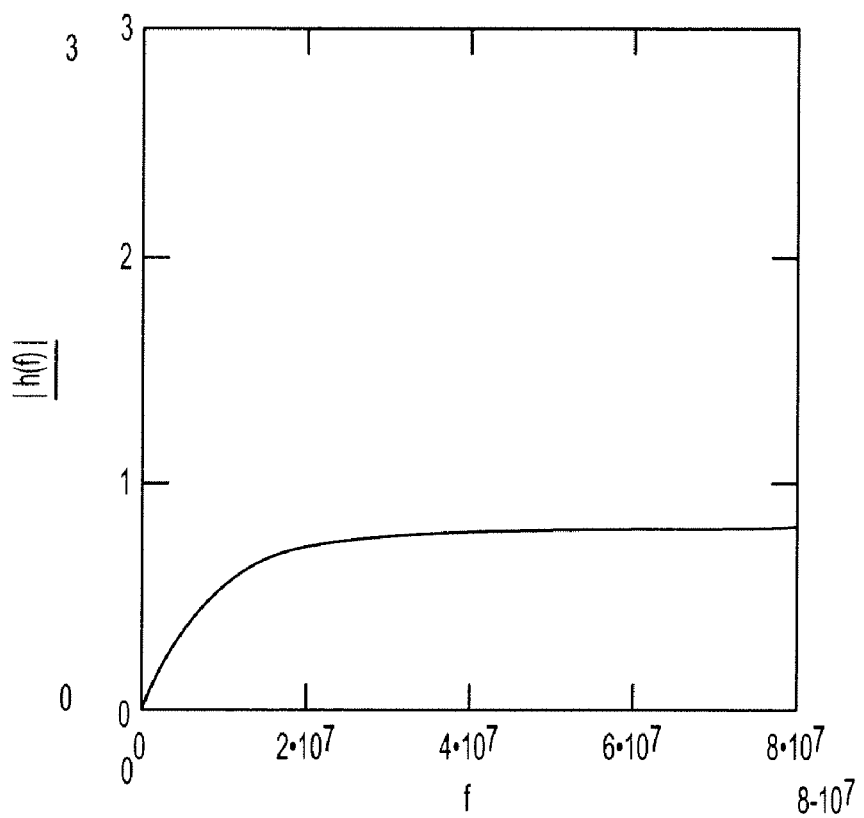
FIG. 3 depicts magnitude of the infinite impulse response filter H(z) used to cancel single pole exponential tail from an avalanche photodiode/charge sensitive amplifier based detector.

FIG. 3 depicts one possible embodiment of the IIR filter. The magnitude of the Fourier Transform of the infinite impulse response filter, H(z), used to cancel the single pole exponential tail from an ideal avalanche photodiode/charge sensitive amplifier based detector.

Figure 4:
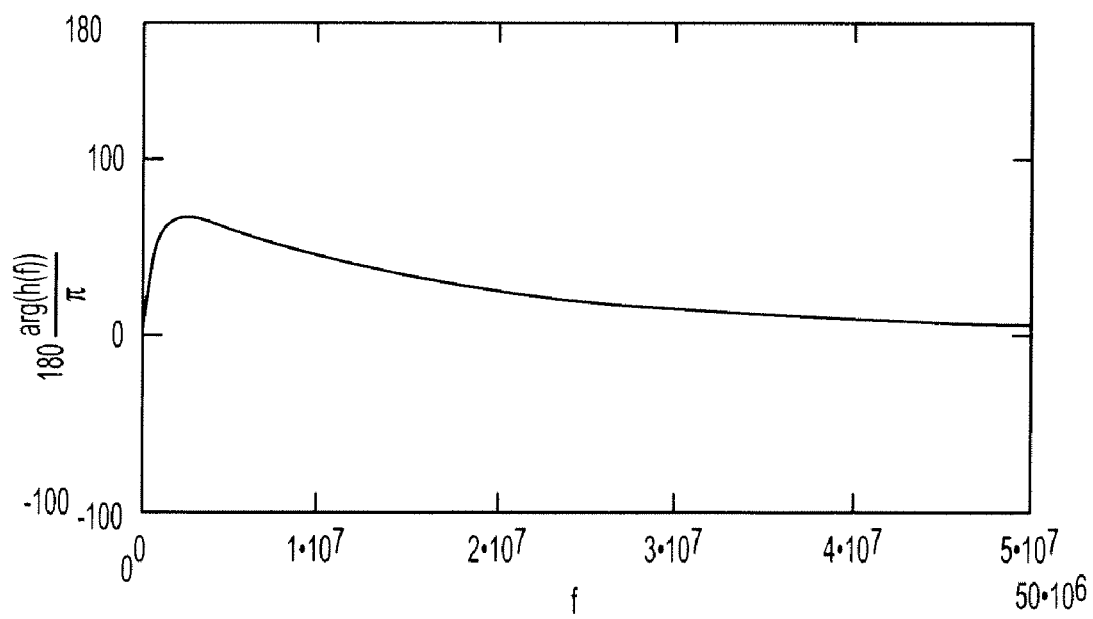
FIG. 4 depicts the ideal phase Fourier spectrum of an infinite impulse response filter H(z) used to cancel the single pole exponential tail from an avalanche photodiode/charge sensitive amplifier based detector.

FIG. 4 depicts the phase response of the Fourier Transform of one embodiment of the infinite impulse response filter, H(z), used to cancel the single pole exponential tail from an ideal avalanche photodiode/charge sensitive amplifier based detector.

A processor as used herein is a device for executing stored machine-readable instructions for performing tasks and may comprise any one or combination of hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

The technology can take the form of an entirely hardware embodiment, an entirely software embodiment or an embodiment containing both hardware and software elements. In one embodiment, the invention is implemented in software, which includes but is not limited to firmware, resident software, microcode, etc. Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium (though propagation mediums in and of themselves as signal carriers are not included in the definition of physical computer-readable medium). Examples of a physical computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. Both processors and program code for implementing each as aspect of the technology can be centralized and/or distributed as known to those skilled in the art.

The above disclosure provides examples and aspects relating to various embodiments within the scope of claims, appended hereto or later added in accordance with applicable law. However, these examples are not limiting as to how any disclosed aspect may be implemented, as those of ordinary skill can apply these disclosures to particular situations in a variety of ways.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C §112, sixth paragraph. In particular, the use of "step of" in the claims herein is not intended to invoke the provisions of 35 U.S.C §112, sixth paragraph.

We claim:

1. A method comprising:
    scanning a subject with a combined magnetic resonance imaging (MRI)/positron emission tomography (PET) scanner having a PET imaging modality and an MR imaging modality;
    using an analog to digital converter to discrete time sample a signal from a photo detector;
    cancelling one or more poles of the signal with a digital infinite impulse response filter implemented with fixed-point arithmetic inside a field programmable gate array to subtract the tail of an integrated energy signal to eliminate high frequency components that may interfere with the MR imaging modality to obtain a modified signal; and
    using the modified signal to generate an image of the subject,
    wherein the infinite impulse response filter z-transform for the field programmable gate array implemented single pole/zero digital filter is described mathematically by the equation $$H(z) = K_1 - \frac{K_2}{1 - K_3 z^{-1}}$$

for an idealized model of a single exponential defined detector signal,
wherein z represents the complex variable $e^{sT}$,
$K_1$ represents a digital constant coefficient associated with the input,
$K_2$ represents a digital constant coefficient,
$K_3$ represents the coefficient associated with the past input and output samples.

2. The method according to claim 1, wherein the signal is approximated as a sum of exponentials.

3. The method according to claim 1, wherein one of the one or more poles is not cancelled, and wherein the method further comprises using the uncancelled pole as an input to an algorithm.

4. The method according to claim 3, wherein the algorithm is a digitial timing algorithm.

5. The method according to claim 3, wherein the algorithm is a crystal localization algorithm.

6. The method according to claim 3, wherein the algorithm is a total energy algorithm.

7. The method according to claim 3, wherein one of the one or more poles is not cancelled when a detected photon count rate is greater than 50 kcps.

8. The method according to claim 1, wherein the photodetector is an avalanche photodiode.

9. The method according to claim 8, wherein the avalanche photodiode is biased in the linear range.

10. The method according to claim 1, further comprising measuring a signal tail remaining in the modified signal on a per photo detector basis or on a multiple combination of photo detectors basis, and using a least squares error fit of the measured signal to tune the digital coefficients of the digital infinite impulse response filter.

11. The method according to claim 10, further comprising storing the tuned digital coefficients in nonvolatile memory or in volatile memory for later PET data acquisitions.

12. The method according to claim 1, wherein prior to using the analog to digital converter to discrete time sample the signal, the method further comprises cancelling one or more poles of the signal with an analog pole/zero filter.

13. The method according to claim 12, further comprising using a sum of exponentials approximation to model a remnant tail of the detector signal remaining after approximate analog pole/zero cancellation.

14. The method according to claim 13, wherein the sum of exponentials approximation uses a predicted statistical mean or expected value of an integrator reset time constant of an application specific integrated circuit (ASIC) charge sensitive amplifier (CSA) as an analog pole/zero circuit time constant.

15. A computer program product for a combined magnetic resonance imaging (MRI)/positron emission tomography (PET) scanner having a PET imaging modality and an MR imaging modality, the product comprising:
a non-transitory computer-readable medium;
a processing module residing on the computer-readable storage medium and operative to cancel one or more poles of a signal from a photo detector with a digital infinite impulse response filter implemented with fixed-point arithmetic to subtract the tail of an integrated energy signal to eliminate high frequency components that may interfere with the MR imaging modality to obtain a modified signal; and
a display module residing on the computer-readable medium and operative to cause the display of an image of a subject based on the modified signal,
wherein the digital infinite impulse response filter employs a z-transform described mathematically by the equation $$H(z) = K_1 - \frac{K_2}{1 - K_3 z^{-1}}$$

for an idealized model of a single exponential defined detector signal,
wherein z represents the complex variable $e^{sT}$,
$K_1$ represents a digital constant coefficient associated with the input,
$K_2$ represents a digital constant coefficient,
$K_3$ represents the coefficient associated with the past input and output samples.

16. The computer program product according to claim 15, wherein the signal is approximated as a sum of exponentials.

17. The computer program product according to claim 15, wherein one of the one or more poles is not cancelled, and wherein the processing module is further operative to use the resulting signal as an input to an algorithm.

18. The computer program product according to claim 17, wherein the algorithm is a digital timing algorithm.

19. The computer program product according to claim 17, wherein the algorithm is a crystal localization algorithm.

20. The computer program product according to claim 17, wherein the algorithm is a total energy algorithm.

21. The computer program product according to claim 15, wherein one of the one or more poles is not cancelled when a detected photon count rate is greater than 50 kcps.

22. The computer program product according to claim 15, wherein the photo detector is an avalanche photodiode.

23. The computer program product according to claim 15, wherein the avalanche photodiode is biased in the linear range.

24. The computer program product according to claim 15, wherein the processing module is further operative to measure a signal tail remaining in the modified signal on a photo detector basis or on a multiple combination of photo detectors basis, and to use a least squares error fit to tune digital coefficients of the digital infinite impulse response filter.

25. The computer program product according to claim 24, wherein the processing module is further operative to store the tuned digital coefficients in a nonvolatile or volatile memory for later PET data acquisitions.

26. A system for a combined magnetic resonance imaging (MRI)/positron emission tomography (PET) scanner having a PET imaging modality and an MR imaging modality, comprising:
a display device for displaying an image of a subject; and
a processor communicatively coupled to the display and operative to provide the image to the display device,
wherein the processor cancels one or more poles of a signal from a photo detector with a digital infinite impulse response filter implemented with fixed-point arithmetic to subtract the tail of an integrated energy signal to eliminate high frequency components that may interfere with the MR imaging modality to obtain a modified signal, and wherein the digital infinite impulse response filter employs a z-transform described mathematically by the equation $$H(z) = K_1 - \frac{K_2}{1 - K_3 z^{-1}}$$

for an ideal model of a single exponential defined detector signal,
wherein z represents the complex variable $e^{sT}$,
$K_1$ resents a digital constant coefficient associated with the input,
$K_2$ represents a digital constant coefficient,
$K_3$ represents the coefficient associated with the past input and output samples.

27. The system according to claim 26, wherein the signal is approximated as a sum of exponentials.

28. The system according to claim 26, wherein one of the one or more poles is not cancelled, and wherein the processor is further operative to use the uncancelled pole as an input to an algorithm.

29. The system according to claim 28, wherein the algorithm is a digital timing algorithm.

30. The system according to claim 28, wherein the algorithm is a crystal localization algorithm.

31. The system according to claim 28, wherein the algorithm is a total energy algorithm.

32. The system according to claim 26, wherein one of the one or more poles is not cancelled when a detected photon count rate is greater than 50 kcps.

33. The system according to claim 26, wherein the photo detector is an avalanche photodiode.

34. The system according to claim 33, wherein the avalanche photodiode is biased in the linear range.

35. The system according to claim 26, wherein the processor is further operative to measure a signal tail remaining in the modified signal on a photo detector basis or on a multiple combination of photo detectors basis, and to use a least squares error fit to tune digital coefficients of the digital infinite impulse response filter.

36. The system according to claim 35, wherein the processor is further operative to store the tuned digital coefficients in a nonvolatile or volatile memory for later PET data acquisitions.

* * * * *